(12) United States Patent
Jinwal et al.

(10) Patent No.: US 9,114,130 B2
(45) Date of Patent: Aug. 25, 2015

(54) COMPOUNDS AND RELATED METHODS FOR TREATMENT OF NEURODEGENERATIVE DISEASES

(71) Applicants: Umesh Jinwal, Tampa, FL (US); Bill Baker, Tampa, FL (US); Laurent Calcul, Tampa, FL (US)

(72) Inventors: Umesh Jinwal, Tampa, FL (US); Bill Baker, Tampa, FL (US); Laurent Calcul, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/271,177

(22) Filed: May 6, 2014

(65) Prior Publication Data

US 2014/0329791 A1    Nov. 6, 2014

Related U.S. Application Data

(60) Provisional application No. 61/819,701, filed on May 6, 2013.

(51) Int. Cl.
*A61K 31/222* (2006.01)
*A61K 31/395* (2006.01)

(52) U.S. Cl.
CPC ............. *A61K 31/395* (2013.01); *A61K 31/222* (2013.01)

(58) Field of Classification Search
CPC .................................................. A61K 31/222
See application file for complete search history.

(56) References Cited

U.S. PATENT DOCUMENTS

| 4,321,262 A | 3/1982 | Burnett |
| 6,103,242 A | 8/2000 | Buckley |
| 8,372,447 B2 | 2/2013 | Doherty et al. |
| 2009/0022821 A1 | 1/2009 | Dev et al. |
| 2013/0184353 A1 | 7/2013 | Dickey et al. |

FOREIGN PATENT DOCUMENTS

| CN | 101386818 B | 1/2011 |
| CN | 102408998 A | 4/2012 |
| CN | 102309528 B | 6/2013 |
| EP | 2319522 A1 | 5/2011 |
| WO | WO-2008/133884 A2 | 11/2008 |
| WO | WO-2012/012798 A2 | 1/2012 |

OTHER PUBLICATIONS

Brunden et al. Nature Reviews, Oct. 2009, vol. 8, pp. 783-793.*
Maschek et al. Tetrahedron, 2012, vol. 68, pp. 9095-9104.*

* cited by examiner

*Primary Examiner* — James D Anderson
(74) *Attorney, Agent, or Firm* — Saliwanchik, Lloyd & Eisenschenk

(57) ABSTRACT

Aspects of the invention pertain to chemical compounds, therapeutic compositions, and methods for treating neurodegenerative diseases, in particular, neurodegenerative diseases associated with abnormal accumulation of protein tau.

6 Claims, 1 Drawing Sheet

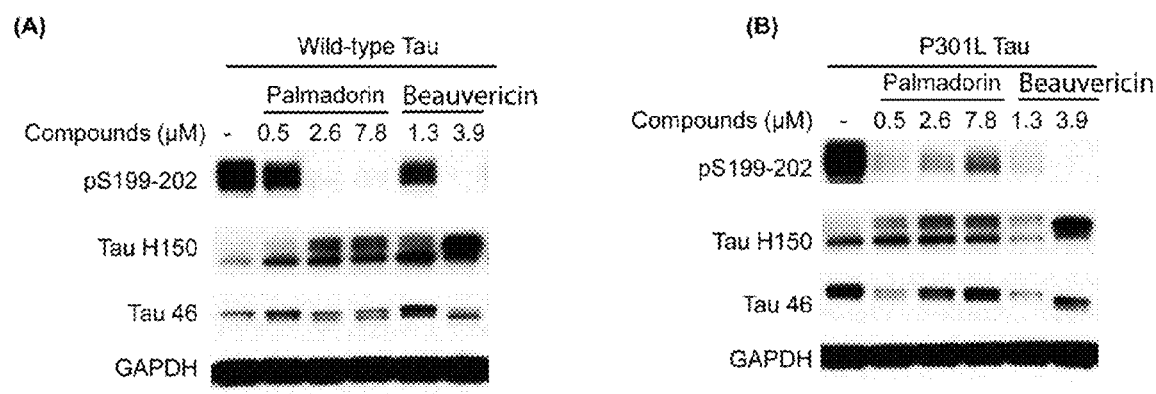

SEQUENCE LISTING

```
<160> NUMBER OF SEQ ID NOS: 6

<210> SEQ ID NO 1
<211> LENGTH: 352
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80
```

-continued

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
            130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Val Tyr Lys Pro Val
            210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
            290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 2
<211> LENGTH: 441
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
                385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
                435                 440

<210> SEQ ID NO 3
<211> LENGTH: 383
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1                   5                   10                  15

Thr Tyr Gly Leu Gly Asp Arg Lys Asp Gln Gly Gly Tyr Thr Met His
                20                  25                  30

```
Gln Asp Gln Glu Gly Asp Thr Asp Ala Gly Leu Lys Ala Glu Glu Ala
         35                  40                  45

Gly Ile Gly Asp Thr Pro Ser Leu Glu Asp Glu Ala Ala Gly His Val
 50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
            100                 105                 110

Ile Pro Ala Lys Thr Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
        130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 4
<211> LENGTH: 758
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30
```

```
Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                     85                  90                  95

Ile Pro Glu Gly Thr Thr Ala Glu Glu Ala Gly Ile Gly Asp Thr Pro
                    100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
                195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
                260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
        290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
                355                 360                 365

Ser Arg Val Pro Gln Leu Lys Ala Arg Met Val Ser Lys Ser Lys Asp
        370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys Tyr Val Ser Ser Val Thr Ser Arg
                435                 440                 445
```

```
Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 5
<211> LENGTH: 776
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60
```

```
Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
             85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
            210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
        290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
        370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
            405                 410                 415

Pro Gly Ser Ser Asp Pro Leu Ile Gln Pro Ser Ser Pro Ala Val Cys
            420                 425                 430

Pro Glu Pro Pro Ser Ser Pro Lys Tyr Val Ser Ser Val Thr Ser Arg
            435                 440                 445

Thr Gly Ser Ser Gly Ala Lys Glu Met Lys Leu Lys Gly Ala Asp Gly
        450                 455                 460

Lys Thr Lys Ile Ala Thr Pro Arg Gly Ala Ala Pro Pro Gly Gln Lys
465                 470                 475                 480
```

-continued

```
Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
        500                 505                 510

Pro Ala Gly Pro Arg Ser Glu Arg Gly Glu Pro Pro Lys Ser Gly Asp
            515                 520                 525

Arg Ser Gly Tyr Ser Ser Pro Gly Ser Pro Gly Thr Pro Gly Ser Arg
    530                 535                 540

Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ser Ala Lys Ser
                565                 570                 575

Arg Leu Gln Thr Ala Pro Val Pro Met Pro Asp Leu Lys Asn Val Lys
            580                 585                 590

Ser Lys Ile Gly Ser Thr Glu Asn Leu Lys His Gln Pro Gly Gly Gly
        595                 600                 605

Lys Val Gln Ile Ile Asn Lys Lys Leu Asp Leu Ser Asn Val Gln Ser
    610                 615                 620

Lys Cys Gly Ser Lys Asp Asn Ile Lys His Val Pro Gly Gly Gly Ser
625                 630                 635                 640

Val Gln Ile Val Tyr Lys Pro Val Asp Leu Ser Lys Val Thr Ser Lys
                645                 650                 655

Cys Gly Ser Leu Gly Asn Ile His His Lys Pro Gly Gly Gly Gln Val
            660                 665                 670

Glu Val Lys Ser Glu Lys Leu Asp Phe Lys Asp Arg Val Gln Ser Lys
        675                 680                 685

Ile Gly Ser Leu Asp Asn Ile Thr His Val Pro Gly Gly Gly Asn Lys
    690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735

Asp Thr Ser Pro Arg His Leu Ser Asn Val Ser Ser Thr Gly Ser Ile
            740                 745                 750

Asp Met Val Asp Ser Pro Gln Leu Ala Thr Leu Ala Asp Glu Val Ser
        755                 760                 765

Ala Ser Leu Ala Lys Gln Gly Leu
    770                 775

<210> SEQ ID NO 6
<211> LENGTH: 412
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80
```

-continued

```
Asp Thr Pro Ser Leu Glu Asp Glu Ala Ala Gly His Val Thr Gln Ala
             85                  90                  95

Arg Met Val Ser Lys Ser Lys Asp Gly Thr Gly Ser Asp Lys Lys
            100                 105                 110

Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
            130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Thr Arg
                180                 185                 190

Glu Pro Lys Lys Val Ala Val Val Arg Thr Pro Pro Lys Ser Pro Ser
                195                 200                 205

Ser Ala Lys Ser Arg Leu Gln Thr Ala Pro Val Pro Met Pro Asp Leu
            210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
                260                 265                 270

Gly Gly Gly Ser Val Gln Ile Val Tyr Lys Pro Val Asp Leu Ser Lys
                275                 280                 285

Val Thr Ser Lys Cys Gly Ser Leu Gly Asn Ile His His Lys Pro Gly
            290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
                340                 345                 350

Ala Lys Ala Lys Thr Asp His Gly Ala Glu Ile Val Tyr Lys Ser Pro
            355                 360                 365

Val Val Ser Gly Asp Thr Ser Pro Arg His Leu Ser Asn Val Ser Ser
            370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410
```

COMPOUNDS AND RELATED METHODS FOR TREATMENT OF NEURODEGENERATIVE DISEASES

CROSS-REFERENCE TO RELATED APPLICATION

This application claims the benefit of U.S. Provisional Application Ser. No. 61/819,701, filed May 6, 2013, which is hereby incorporated by reference in its entirety.

BACKGROUND

Intracellular aggregation of abnormal species of phosphorylated tau (protein tau) is a major pathologic feature of a family of neurodegenerative diseases collectively referred to as the tauopathies. Tau normally functions to stabilize microtubules in neurons; however, it pathologically aggregates more than 15 neurodegenerative diseases, including Alzheimer's disease (AD) and Parkinson's disease. The most common tauopathy is Alzheimer's disease, in which paired helical filaments (PHFs) of mis-folded protein tau aggregates in neurofibrillary tangles, in dystrophic neuritis of senile plaques, and in cell processes in the neuropil. Abnormal accumulation of protein tau is closely linked with postsymptomatic progression in Alzheimer's disease. Abnormal accumulation of protein tau in the cytoplasm of neuronal and glial cells also represents major structural hallmarks in the pathology of Pick's disease, corticobasal degeneration, and progressive supranuclear palsy.

At present, researchers on the development of therapeutics for tauopathies focus primarily on agents that prevent abnormal phosphorylation or aggregation of tau proteins. However, it has been discovered that while aggregation of hyperphosphorylated protein tau is visible evidence of tauopathies, these neurofibrillary tangles appear to be less toxic than soluble intermediates of protein tau. High levels of tau intermediates, particularly aberrant tau species failed to be cleared from cells, cause cognitive dysfunction in AD and tauopathies. Therefore, agents that degrade or destabilize tau intermediates, clear aberrant tau species from cells, or otherwise reduce intracellular tau levels, are promising therapeutics for AD and tauopathies.

Existing therapeutics for the treatment tauopathies (such as AD) only demonstrate limited efficacy; as such, additional therapeutics for the treatment of tauopathies are needed.

BRIEF SUMMARY

Aspects of the invention provide chemical compounds for treating neurodegenerative diseases, in particular, neurodegenerative diseases associated with abnormal accumulation of protein tau.

One aspect of the invention provides a method of reducing intracellular tau levels comprising administering, to cells comprising protein tau, an effective amount of compound A:

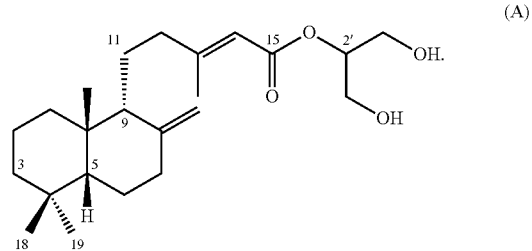

(A)

In another aspect, the invention provides a method of reducing intracellular tau levels comprising administering, to cells comprising protein tau, an effective amount of compound B:

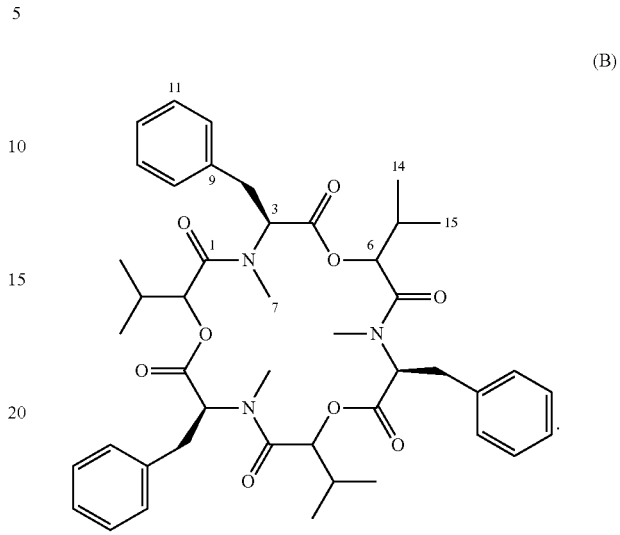

(B)

In some embodiments of aspects of the invention, the cells are in a subject, such as a human, in need of treatment for a neurodegenerative disease. The neurodegenerative disease may be a tauopathy. In some embodiments, the neurodegenerative disease is selected from Alzheimer's disease, Parkinson's disease, frontotemporal dementia, frontotemporal dementia with Parkinsonism, frontotemporal lobe dementia, pallidopontonigral degeneration, progressive supranuclear palsy, multiple system tauopathy, multiple system tauopathy with presenile dementia, Wilhelmsen-Lynch disease, Pick's disease, or Pick's disease-like dementia. In one embodiment, the neurodegenerative disease is Alzheimer's disease.

In additional aspects, the invention provides pharmaceutical compositions comprising any of compounds A, B, and combinations thereof.

BRIEF DESCRIPTION OF THE DRAWINGS

FIG. 1 shows a western blot analysis of phosphorylated tau following Palmadorin M and Beauvericin treatment in HeLa cells transfected with (A) wild type human tau and (B) mutant P301L human tau.

BRIEF DESCRIPTION OF THE SEQUENCES

SEQ ID NO:1 is an amino acid sequence of a tau protein isoform (tau 352) useful according to aspects of the invention.

SEQ ID NO:2 is an amino acid sequence of a tau protein isoform (tau 441) useful according to aspects of the invention.

SEQ ID NO:3 is an amino acid sequence of a tau protein isoform (tau 383) useful according to aspects of the invention.

SEQ ID NO:4 is an amino acid sequence of a tau protein isoform (tau 758) useful according to aspects of the invention.

SEQ ID NO:5 is an amino acid sequence of a tau protein isoform (tau 776) useful according to aspects of the invention.

SEQ ID NO:6 is an amino acid sequence of a tau protein isoform (tau 412) useful according to aspects of the invention.

DETAILED DESCRIPTION

Aspects of the invention provide chemical compounds and compositions for treating neurodegenerative diseases, in particular, neurodegenerative diseases associated with abnormal accumulation of protein tau.

In one aspect, the invention provides compounds A and B, or salts thereof:

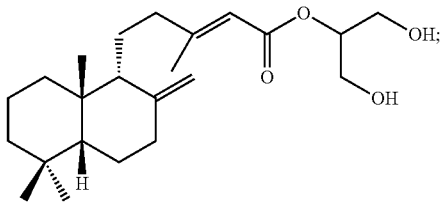

Palmadorin M
Chemical Formula: $C_{23}H_{38}O_4$
Molecular Weight: 378.5454

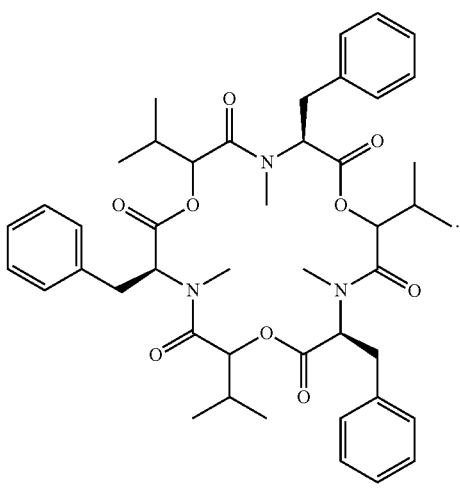

Chemical Formula: $C_{45}H_{57}N_3O_9$
Molecular Weight: 783.9488

Beauvericin

In one embodiment, the invention provides an isolated or substantially pure compound A, or a salt thereof,

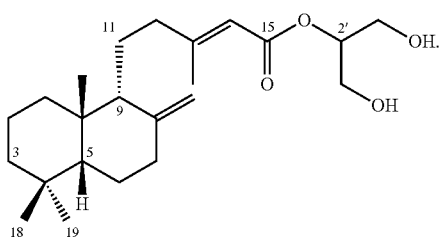

In one embodiment, the invention provides an isolated or substantially pure compound B, or a salt thereof,

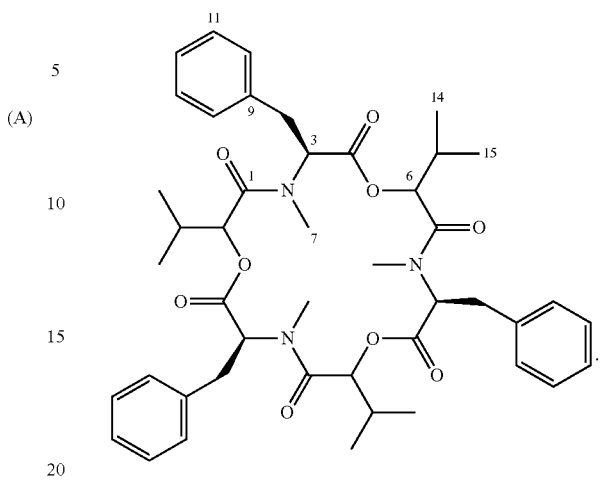

In certain embodiments, the invention pertains to the uses of compound A (palmadorin M) and/or compound B (beauvericin), or salts thereof, for treating neurodegenerative diseases, in particular, neurodegenerative diseases associated with abnormal accumulation of protein tau.

In some embodiments, the compounds of the present invention are at least 75% pure, preferably at least 90% pure, more preferably are more than 95% pure, and most preferably are more than 99% pure (substantially pure). The compounds of the present invention can also be synthesized.

The compounds and compositions of the present invention, through administration to a subject, are useful for treating or ameliorating neurodegenerative diseases or conditions, in particular, neurodegenerative diseases or conditions associated with abnormally high levels of protein tau and/or abnormal accumulation of protein tau in neurons. In some embodiments, the compounds and compositions are useful to treat or ameliorate Alzheimer's disease or Parkinson's disease.

In one aspect, the invention provides methods for treating or ameliorating a neurodegenerative disease or condition, particularly a disease or condition associated with abnormally high levels of protein tau and/or abnormal accumulation of protein tau in neurons, wherein the method comprises administering, to a subject in need of such treatment, an effective amount of a composition comprising a compound selected from compound A and compound B, or salts thereof.

Another aspect of the invention provides a method of reducing intracellular tau levels comprising administering, to cells comprising protein tau, an effective amount of compound A:

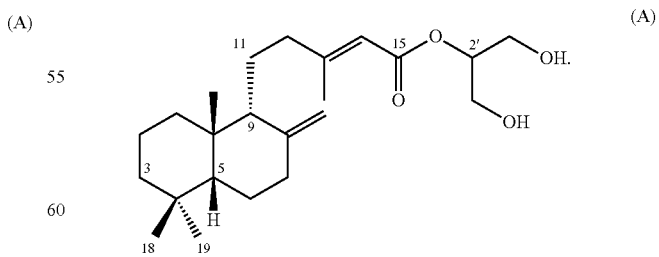

In another aspect, the invention provides a method of reducing intracellular tau levels comprising administering, to cells comprising protein tau, an effective amount of compound B:

(B)

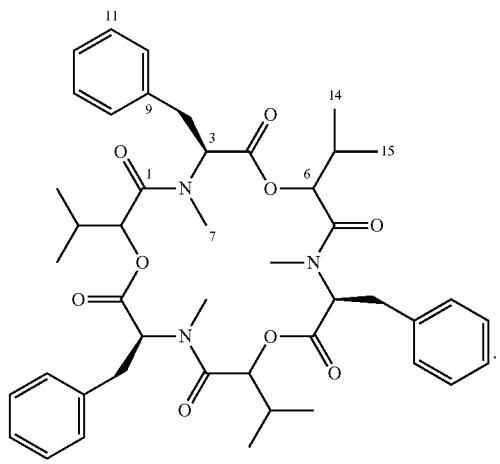

In yet another aspect, the invention provides a method of reducing intracellular tau levels comprising administering, to cells comprising protein tau, an effective amount of compounds selected from compound A (Palmadorin M) and compound B (Beauvericin), and combinations thereof.

The term "subject," as used herein, describes an organism, including mammals, to which treatment with the compositions and compounds according to the subject invention can be administered. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

The term "tau protein" or any grammatical variation thereof (e.g., protein tau and tau etc.), as used herein, refers generally to any protein of the microtubule-associated tau protein family. Members of the tau family share the common features of a characteristic N-terminal segment, sequences of approximately 50 amino acids inserted in the N-terminal segment, a characteristic tandem repeat region consisting of 3 or 4 tandem repeats of 31-32 amino acids, and a C-terminal tail. Tau proteins of the present invention may be in a form of soluble tau intermediates, functional, aberrant, abnormally-truncated, mis-folded or mis-processed tau, and phosphorylated tau.

In some embodiments, tau protein of the invention is of mammalian origin, and more preferably, of human origin. Specifically, tau proteins of the subject invention include microtubule-associated protein translated from the human chromosomal sequence of GenBank Accession No. AH005895 and naturally-occurring mammalian variants or isoforms thereof. Six human brain tau isoforms are currently known, including tau352 (GenBank Accession No. NP_058525) (SEQ ID NO:1), tau441 (GenBank Accession No. NP_005901) (SEQ ID NO:2), tau383 (GenBank Accession No. NP_058518) (SEQ ID NO:3), tau758 (GenBank Accession No. NP_058519) (SEQ ID NO:4), tau776 (GenBank Accession No. NP_001116538) (SEQ ID NO:5), and tau412 (GenBank Accession No. NP_001116539) (SEQ ID NO:6).

The term "treatment" or any grammatical variation thereof (e.g., treat, treating and treatment etc.), as used herein, includes but is not limited to, ameliorating or alleviating a symptom of a disease or condition, reducing, suppressing, inhibiting, lessening, or affecting the progression, severity, and/or scope of a condition, chance of re-occurrence or returning of a disease after a remission. For instance, the term "treatment" includes (i) ameliorating a symptom associated with a neurodegenerative disease in a patient diagnosed with the neurodegenerative disease; and/or (ii) relieving (such as attenuating the progress of) or remedying a neurodegenerative disease in a patient diagnosed with the neurodegenerative disease.

In some embodiments, the treatment methods of the present invention reduce tau levels and/or improve tau clearance. Normal, functional tau is less affected by clearance pathways in the cell than aberrant tau. In one embodiment, the treatment methods of the present invention modulate tau clearance by selectively targeting abnormal tau.

In an embodiment, the therapeutic composition is administered to a human subject who has symptoms of, or is diagnosed with, a neurodegenerative disease. In some embodiments, the therapeutic composition is administered to a human subject who has symptoms of, or is diagnosed with, a neurodegenerative disease associated with abnormal accumulation of protein tau. For instance, the therapeutic composition is administered to a human subject who has elevated levels of soluble protein tau and/or hyperphosphorylated protein tau in the nervous system, such as in the brain or cytoplasm of neuronal and glial cells. In addition, the therapeutic composition is administered to a human subject who exhibits pathologic features such as neurofibrillary tangles or senile plaques in neuronal cells and/or cell processes. In a specific embodiment, the therapeutic composition is administered to a human subject who has symptoms of, or is diagnosed with, Alzheimer's disease.

The identification of subjects who are in need of treatment for a neurodegenerative disease is well within the knowledge and ability of one skilled in the art. By way of example, a clinician skilled in the art can readily identify, by the use of clinical tests, neurologic and physical examination, and medical/family history, those patients who are suffering from a neurodegenerative disease as well as those who are predisposed to developing a neurodegenerative disease and thus readily determine if an individual is in need of treatment. For instance, neurofibrillary tangles or senile plaques present in neuronal cells and/or cell processes can be determined using electron microscopy (EM) or other clinical techniques known in the art. In addition, spinal fluid or cerebral fluid samples or tissues samples from hippocampal tissue or frontal cortex tissue samples may be obtained from a subject and levels of protein tau present in the samples can be determined using routine techniques such as enzyme-linked immunosorbant assay (ELISA), western blot, and immunological assays.

The compounds and compositions of the present invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject. In a one embodiment, the compounds and compositions of the subject invention are administered orally.

The term "effective amount" or "therapeutically effective amount," as used herein, refers to an amount that is capable of treating or ameliorating a disease or condition or otherwise capable of producing an intended therapeutic effect. For instance, the effective amount of the compounds and compositions of the present invention is an amount capable of reducing levels of protein tau in a subject. In certain embodiments, the effective amount enables a 5%, 25%, 50%, 75%, 90%, 95%, 99% and 100% reduction of levels of protein tau (e.g. soluble protein tau intermediates and/or aberrant protein tau) in a subject.

The amount of the therapeutic or pharmaceutical composition which is effective in treatment of a neurodegenerative disease will depend on the nature of the disease, condition or disorder and can be determined by standard clinical techniques. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 20 mg/kg; and aerosol, 0.01 to about 20 mg/kg of animal (body) weight.

Once improvement of the subject's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Subjects may however require intermittent treatment on a long-term basis upon any recurrence of disease symptoms.

In addition, in vitro assays may optionally be employed to help identify optimal dosage ranges. The precise dose to be employed in the formulation/composition will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

The compounds and compositions of the present invention can be used to treat or ameliorate neurodegenerative diseases including, but not limited to, Alzheimer's disease, Parkinson's disease, Amyotrophic lateral sclerosis (ALS), Huntington's disease, multiple sclerosis, Pick's disease, fronto temporal dementia, cortico-basal degeneration, progressive supranuclear palsy, Creutzfeldt-Jakob disease, Gerstmann-Straussler-Scheinker syndrome, and Kuru.

The compounds and compositions of the present invention can also be used to treat or ameliorate neurodegenerative diseases including, but not limited to, Down's syndrome, Argyrophilic grain disease, parkinsonism dementia complex of Guam, non-Guamanian motor neurone disease with NFT, Niemann-Pick disease type C, subacute sclerosing panencephalitis, postencephalitic parkinsonism, dementia pugilistica, myotonic dystrophy, prion protein amyloid antipathy, and Hallervorden-Spatz disease.

The compounds and compositions of the present invention are particularly useful to treat or ameliorate a neurodegenerative disease involving tau pathologies (i.e., tauopathies) including, but not limited to, Alzheimer's disease, Parkinson's disease, frontotemporal dementia, frontotemporal dementia with Parkinsonism, frontotemporal lobe dementia, pallidopontonigral degeneration, progressive supranuclear palsy, multiple system tauopathy, multiple system tauopathy with presenile dementia, Wilhelmsen-Lynch disease, Pick's disease, and Pick's disease-like dementia.

Specifically, the compounds and compositions of the present invention are particularly useful to treat or ameliorate a disease or condition arising, at least in part, from abnormally high levels of protein tau in the nervous system, such as in cytoplasm of neuronal and glial cells and in neuronal and glial cell processes. Thus, the subject invention is particularly useful for treatment of neurodegenerative diseases and disorders, in which reduction of levels of protein tau in the nervous system would be beneficial.

In addition, the compounds and compositions of the subject invention are useful for alleviating or attenuating symptoms arising from or associated with neurodegenerative diseases, including cognitive dysfunction, impaired memory, impaired mental capacities, emotional disturbances, speech dysfunction, incontinence, tremor, postural instability, rigidity or stiff movement, muscle paralysis, and pain.

In additional aspects, the invention provides pharmaceutical compositions comprising a therapeutically effective amount of any of compounds A and/or B and a pharmaceutically acceptable carrier or adjuvant.

The terms "pharmaceutically acceptable", "physiologically tolerable" and grammatical variations thereof, as used herein, include compositions, carriers, diluents and reagents, are used interchangeably, and represent that the materials are capable of administration to or upon a subject such as mammal.

The term "carrier" refers to an adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Particularly preferred pharmaceutical carriers for treatment of or amelioration of a neurodegenerative disease are carriers that can penetrate the blood/brain barrier.

Suitable carriers also include ethanol, dimethyl sulfoxide, glycerol, silica, alumina, starch, sorbitol, inosital, xylitol, D-xylose, mannitol, powdered cellulose, microcrystalline cellulose, talc, colloidal silicon dioxide, calcium carbonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents.

The amount of active ingredient (i.e., one or more of compounds A or B) that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

The compounds and compositions can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the present invention. In general, the compositions of the present invention will be formulated such that an effective amount of the bioactive compound(s) is/are combined with a suitable carrier in order to facilitate effective administration of the composition.

The therapeutic or pharmaceutical compositions of the invention can also be formulated as neutral or salt forms.

Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The preparation of a pharmacological composition that contains active ingredients dissolved or dispersed therein is well understood in the art and need not be limited based on formulation. Typically such compositions are prepared as injectables, either as liquid solutions or suspensions; however, solid forms suitable for solution, or suspensions, in liquid prior to use also can be prepared. The preparation also can be emulsified, such as oil-in-water emulsion.

The compounds and compositions of the present invention in prescription amounts can be readily made into any form of drug, suitable for administering to humans or other animals. Suitable forms include, for example, tinctures, decoctions, and dry extracts. These can be taken orally, applied through venous injection, mucous membranes or inhalation. The active ingredient(s) can also be formulated into capsules, powder, pallets, pastille, suppositories, oral solutions, pasteurized gastroenteric suspension injections, small or large amounts of injection, frozen powder injections, pasteurized powder injections and the like.

EXAMPLES

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Palmadorin M Extraction and Characterization 600 g of freeze-dried Antarctic nudibranchs, *Austrodoris kerguelenensis*, collected by hand via SCUBA off the Palmer Station in the Western Antarctic Peninsula (3-40 m depth range), were first extracted by DCM/MeOH (1:1) then EtOAc/H$_2$O (1:1). Both resulting extracts were combined and fractionated by normal phase MPLC using gradient conditions from 100% hexanes to 100% ethyl acetate to 100% methanol. The separation provided 10 MPLC fractions. The last 8 fractions were combined and purified by reversed-phase semi-preparative HPLC (40-100% MeOH—H$_2$O over 70 minutes) to provide 16 fractions. Fraction 13 (47 min) yielded 10.1 mg of palmadorin M (Maschek J. A., 2011 et Maschek J. A. et al., 2012).

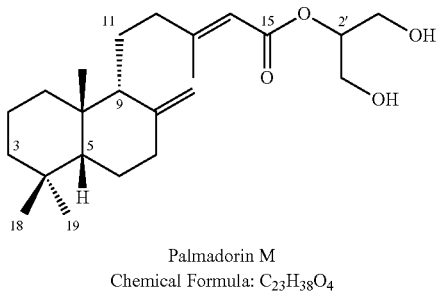

Palmadorin M
Chemical Formula: C$_{23}$H$_{38}$O$_4$

Colorless oil; $[\alpha]_D^{20}$ −18 (c 0.1, CHCl$_3$); UV (MeOH) λmax (ε) 230 (4.38) nm; IR (thin film) 3429 (br), 2935, 1696, 1645, 1214 cm$^{-1}$; $^1$H NMR (500 MHz, CDCl$_3$) 5.72 (1H, s, H-14), 4.93 (1H, s, H-2'), 4.71 (1H, t, H-17b), 4.52 (1H, t, H-17a), 3.83 (2H, m, H$_2$-1'), 3.83 (2H, m, H$_2$-3'), 2.18 (1H, m, H-7b), 2.15 (3H, s, H$_3$-16), 2.04 (1H, m, H-7a), 2.04 (1H, m, H-12b), 1.87 (1H, m, H-12a), 1.70 (1H, m, H-11b), 1.63 (1H, m, H-2b), 1.62 (1H, m, H-6b), 1.53 (1H, m, H-1b), 1.51 (1H, m, H-9), 1.47 (1H, m, H-11a), 1.44 (1H, m, H-2a), 1.42 (1H, m, H-3b), 1.29 (1H, m, H-6a), 1.28 (1H, m, H-5), 1.18 (1H, m, H-3a), 1.06 (1H, m, H-1a), 0.92 (3H, s, H$_3$-20), 0.88 (3H, s, H$_3$-19), 0.81 (3H, s, H$_3$-18); $^{13}$C NMR (125 MHz, CDCl$_3$) 166.8 (C-15), 163.2 (C-13), 148.7 (C-8), 114.5 (C-14), 109.9 (C-17), 74.2 (C-2'), 62.3 (C-1'), 62.3 (C-3'), 57.8 (C-9), 45.8 (C-5), 42.6 (C-3), 39.8 (C-12), 38.0 (C-10), 36.7 (C-1), 33.4 (C-19), 33.2 (C-4), 31.5 (C-7), 24.7 (C-11), 23.5 (C-6), 22.3 (C-20), 22.1 (C-18), 19.4 (C-16), 19.1 (C-2); HRESIMS m/z 401.2648 [M+Na]$^+$ (C$_{23}$H$_{38}$NaO$_4$ requires 401.2668).

Example 2

Beauvericin Extraction and Characterization

Fungi Collection, Culture Preparation, Isolation and Scale Up:

Segments of approximately 1-2 mm$^2$ of mangrove samples were plated on malt extract freshwater agar. Fungal growth was examined every day for two weeks and then twice a week for at least one month for isolation of pure fungal strain. Pure fungal cultures were grown for scale up to 2 L total volume in liquid medium which contained 1% w/v glucose, 0.1% w/v yeast extract and 0.2% w/v peptone (3 weeks) for extraction, separation and pure metabolite identification (Calcul et al. 2013)

Beauvericin:

2.3 g from a freeze-dried scale up of fungus strain collection #EG09-15B-2, isolated from the Florida Everglades bark of *Coccoloba uvifera*, was extracted by MeOH. The methanolic extract was separated by reverse phase MPLC using gradient from H$_2$O/10% MeOH to 100% MeOH to give 6 fractions. Fraction 5 was selected to be further chromatographied by normal phase MPLC using a gradient from 100% hexane to 100% EtOAc and provided 6 fractions. Fraction 4 was purified on reverse phase semi-preparative HPLC using isocratic H$_2$O/55% ACN yielding 206.2 mg of Beauvericin (trimer). (Beau J. 2012)

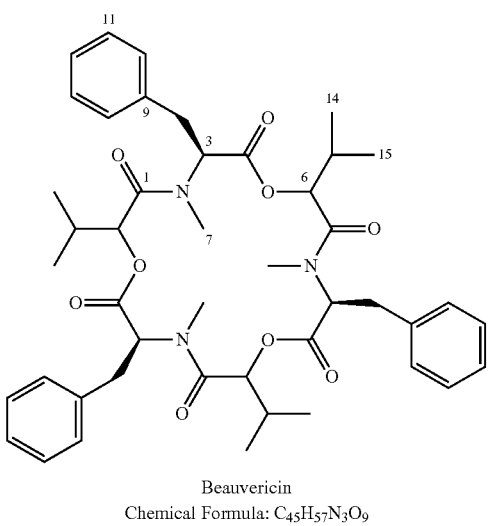 [SMILES: CC(C)C1OC(=O)[C@H](Cc2ccccc2)N(C)C(=O)C(C(C)C)OC(=O)[C@H](Cc2ccccc2)N(C)C(=O)C(C(C)C)OC(=O)[C@H](Cc2ccccc2)N(C)C1=O]

Beauvericin
Chemical Formula: C$_{45}$H$_{57}$N$_3$O$_9$

Colorless film; $^1$H NMR (500 MHz, CDCl$_3$) 7.26-7.14 (3H, m, H-12), 7.26-7.14 (6H, m, H-11), 7.26-7.14 (6H, m, H-10), 5.62 (3H, s, H-6), 4.81 (3H, d, H-3), 3.39 (3H, dd, H-8a), 3.03 (9H, s, H-7), 2.93 (3H, dd, H-8b), 1.93 (3H, dq, H-13), 0.78 (9H, d, H-14), 0.35 (9H, d, H-15); $^{13}$C NMR (125 MHz, CDCl$_3$) 170.0 (C-1), 169.9 (C-4), 136.4 (C-9), 128.7 (C-11), 128.5 (C-10), 126.8 (C-12), 75.7 (C-6), 56.8 (C-3), 34.7 (C-7), 31.9 (C-8), 29.7 (C-13), 18.4 (C-14), 17.1 (C-15); LRESIMS m/z 784.4 [M+H]$^+$—Note: the $^1$H and $^{13}$C NMR data matched to the data from the literature (Gupta, S. et al. 1991);

Example 3

Palmadorin M and Beauvericin Preferentially Reduce Phosphorylated Tau

Compounds effects on tau activity/level were determine by a previously described method (Jinwal et al *J. Neurosci.* 2009 Sep. 30; 29(39):12079-88). In brief, human tau transfected HeLa Cells were treated with Compounds for 24 hours. Cells were harvested by using MPER reagent containing protease inhibitor and phosphatase inhibitor. Samples were analyzed by western blot. pS199-202 antibody was used to detect phospho tau level. Total tau levels were detected by tau H-150 &/or tau 46 antibodies.

HeLa cells were transfected with wild-type human tau (A) and mutant P301L human tau (B) (FIG. 1). After 24 hours, cells were treated with either palmadorin M or beauvericin for 24 hours. Western blot analysis of samples showed potent reduction in phosphorylated (pS199-202) wild type and mutant P301L tau at various doses of palmadorin M and beauvericin. Tau H-150 antibody tested for N-terminal tau showed increase in tau level. Tau 46 antibody tested for C-terminal tau showed moderate change in tau level.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Maschek J. A. "Chemical Investigation of the Antarctic Marine Invertebrates *Austrodoris kerguelenensis* & *Dendrilla membranosa* and the Antarctic Red Alga *Gigartina skottsbergii*" Ph. D. Thesis, Department of Chemistry, College of Art and Sciences, University of South Florida, Tampa, Fla., USA, 7 Jun. 2011.
Maschek J. A. 2012, *Tetrahedron*, 9095-9104.
Beau J. "Drug Discovery from Floridian Mangrove Endophytes" Ph D. Thesis, Department of Chemistry, College of Art and Sciences, University of South Florida, Tampa, Fla., USA, 12 Jul. 2012.
Gupta S. et al. *Mycopathologia*, 1991, 185-189
Calcul L. et al. Mar. Drugs, 2013, 5036-5050.

We claim:

1. A method of reducing intracellular tau phosphorylation levels, wherein the method comprises administering, to cells comprising phosphorylated protein tau, an effective amount of compound A:

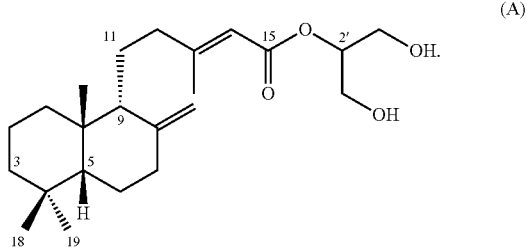

2. The method according to claim 1, wherein the cells are in a subject in need of treatment for a neurodegenerative disease.

3. The method of claim 2, wherein the neurodegenerative disease is a tauopathy.

4. The method of claim 3, wherein the subject is a human.

5. The method of claim 4, wherein the neurodegenerative disease is selected from Alzheimer's disease, Parkinson's disease, frontotemporal dementia, frontotemporal dementia with Parkinsonism, frontotemporal lobe dementia, pallidopontonigral degeneration, progressive supranuclear palsy, multiple system tauopathy, multiple system tauopathy with presenile dementia, Wilhelmsen-Lynch disease, Pick's disease, or Pick's disease-like dementia.

6. The method of claim 4, wherein the neurodegenerative disease is Alzheimer's disease.

\* \* \* \* \*